012# United States Patent [19]

Doyle et al.

[11] Patent Number: 4,471,152

[45] Date of Patent: Sep. 11, 1984

[54] SEPARATION OF OLEFIN MIXTURES BY CU (I) COMPLEXATION

[75] Inventors: Gerald Doyle, Whitehouse Station; Roy L. Pruett, New Providence; David W. Savage, Lebanon; W. S. W. Ho, Westfield, all of N.J.

[73] Assignee: Exxon Research and Engineering Co., Florham Park, N.J.

[21] Appl. No.: 492,174

[22] Filed: May 6, 1983

[51] Int. Cl.³ .............................................. C07C 7/16
[52] U.S. Cl. .................................... 585/848; 585/845
[58] Field of Search .............. 585/843, 844, 845, 846, 585/847, 848, 849

[56] References Cited

U.S. PATENT DOCUMENTS

| 3,401,112 | 9/1968 | Dunlop et al. | 206/306 |
|---|---|---|---|
| 3,518,323 | 6/1970 | Pine et al. | 260/683.15 |
| 3,531,539 | 9/1970 | Tidwell et al. | 260/677 |
| 3,754,047 | 8/1973 | Long et al. | 260/677 |
| 3,755,487 | 8/1973 | Jahnig et al. | 260/677 |
| 4,242,530 | 12/1980 | Smith, Jr. | 585/510 |
| 4,279,874 | 7/1981 | Doyle | 423/246 |
| 4,313,016 | 1/1982 | Manning | 585/832 |
| 4,347,066 | 8/1982 | Doyle | 55/56 |
| 4,385,005 | 5/1983 | Doyle | 585/845 |

OTHER PUBLICATIONS

W. Partenheimer et al., "The Syntheses of Some New Silver Olefin Compounds.", Inorg. Chem., vol. 11, pp. 2840–2841, (1972).

*Primary Examiner*—Delbert E. Gantz
*Assistant Examiner*—A. Pal
*Attorney, Agent, or Firm*—James H. Takemoto; Edward H. Mazer

[57] ABSTRACT

A process for separating a gaseous alkene mixture into components thereof which comprises contacting the gaseous alkene mixture with a cuprous complex of the formula $[Cu(facac)]_x L_y$ where facac is a fluorinated acetylacetonate and L is a stabilizing agent in an organic solvent wherein L is displaced by alkene. Cuprous complexes containing alkene can then be separated provided that the separation factor between alkene complex to be separated and other alkene complexes is at least about 1.05.

11 Claims, 4 Drawing Figures

SEPARATION OF OLEFIN MIXTURES BY CU (I) COMPLEXATION

BACKGROUND OF THE INVENTION

This invention relates to the separation of alkene mixtures. More particularly, mixtures of alkenes are separated by formation of complexes with a cuprous fluorinated acetylacetonate followed by separation of the complexes based on separation factors. The present invention is especially useful for separating mixtures of linear 1-alkenes, branched 1-alkenes, and linear and branched internal alkenes.

It is known that certain cuprous salts form complexes with olefins. U.S. Pat. No. 3,401,112 describes a process for separating hydrocarbon mixtures of differing degrees of unsaturation and isomeric unsaturated hydrocarbons using a cuprous salt of the formula CuXA where XA is the anion of an oxy-acid. U.S. Pat. Nos. 3,754,047 and 3,755,487 disclose the use of a cuprous salt for complexing ligands such as olefins, aromatics, acetylenes, CO and the like from a solvent containing high boiling aromatic compounds. Sorbent materials are cuprous salts of weakly basic acids, e.g., $CuAlCl_4$, $CuBF_4$, $CuPF_6$ and $CuOOCCF_3$. Inorganic Chemistry, 11, 2840 (1972) teaches the preparation of Ag(I) complexes containing hexafluoroacetylacetone and olefins. The preparation occurs in aqueous medium using soluble Ag(I) salts. U.S. Pat. No. 4,279,874 relates to a process for removing CO from a gas stream which comprises contacting the gas stream with an absorbent solution containing a Cu(I) halogenated acetylacetonate complex thereby removing CO as a CO-containing complex. U.S. Pat. No. 4,347,066 describes a process for removing CO and unsaturated hydrocarbons from gas streams using cuprous oxalate complexes.

In the area of separating olefin mixtures, U.S. Pat. No. 3,518,323 relates to a process for separating isobutylene from n-butylene mixtures by selectively dimerizing the isobutylenes using a supported nickel oxide catalyst. U.S. Pat. No. 3,531,539 discloses a process for separating isobutene from a feedstream containing n-butenes and other hydrocarbons by a selective separation process employing molecular sieves having a pore size of about 8.0 to 8.2 Å. U.S. Pat. No. 4,242,530 describes the separation of an isoolefin from an n-olefin using a fixed bed acidic cation exchange resin by dimerizing the isoolefin. The catalyst is packed in a distillation column thereby providing vapor and liquid phase contact. U.S. Pat. No. 4,313,016 teaches a process for removing isobutene from $C_4$ hydrocarbon streams by passing the streams through a cation exchange resin at 50° to 80° C. wherein isobutene is oligomerized and separated.

SUMMARY OF THE INVENTION

It has been discovered that alkene mixtures can be separated using cuprous fluorinated acetylacetonate complexes based on differences in complexing strength of the respective alkenes. In one aspect of the invention, there is provided a process for separating a linear 1-alkene from a gaseous alkene mixture containing at least one linear 1-alkene of the formula $CH_2=CHR^1$ where $R^1$ is H or $C_1-C_6$ alkyl and at least one other alkene of the formula $R^2R^3C=CR^4R^5$ where $R^2$ to $R^5$ are independently H or $C_1-C_6$ alkyl with the proviso that at least two of $R^2$ to $R^5$ are not H, which comprises: contacting the alkene mixture at a temperature sufficient to maintain the mixture in a gaseous state with a solution of a cuprous fluorinated acetylacetonate complex in an organic solvent, said complex having the formula $[Cu(facac)]_xL_y$ where facac is $R_6$ is $C_1-C_6$ fluoralkyl, $C_1-C_8$ alkyl, $C_4-C_6$ heterocycle containing O, S or N or $C_6-C_{10}$ aryl, $R^7$ is H or $C_1-C_6$ alkyl with the proviso that $R^6$ and $R^7$ together with the carbons to which they are attached may be joined together to form a $C_6$ ring, n is an integer from 1 to 8, x and y are 1 or 2, and L is a stabilizing agent, said stabilizing agent being an unsaturated compound containing at least one non-aromatic unsaturation and being a liquid at the reaction temperature, wherein the stabilizing agent L is displaced and a mixture of complexes of the formulae $[Cu(facac)]_x(CH_2=CHR^1)_y$ and $[Cu(facac)]_x(R^2R^3C=CR^4R^5)_y$ is formed; and separating the complex of the formula $[Cu(facac)]_x(CH_2=CHR^1)_y$ provided that the separation factor defined as the ratio of $$\frac{[[Cu(facac)]_x(CH_2=CHR^1)_y]}{[[Cu(facac)]_x(R^2R^3C=CR^4R^5)_y]}$$

at equivalent partial pressure of alkene is at least about 1.05.

Another aspect of the invention relates to a process for separating a gaseous mixture of alkenes of the formula $(R^2R^3C=CR^4R^5)^m$ where $R^2$ to $R^5$ are defined above and m is the number of different alkenes in the mixture which comprises contacting the alkene mixture at a temperature sufficient to maintain the mixture in a gaseous state with a solution of a cuprous fluorinated acetylacetonate in an organic solvent, said complex having the formula $[Cu(facac)]_xL_y$ where facac, x, y and L are defined above wherein stabilizing agent L is displaced and a mixture of m complexes of the formulae $[Cu(facac)]_x(R^2R^3C=CR^4R^5)_y$ is formed; and separating a complex of the formula $[Cu(facac)]_x[(R^2R^3C=CR^4R^5)^b]_y$ where b represents one complex in the set of m complexes formed provided that the separation factor defined as the ratio of $$\frac{[[Cu(facac)]_x[(R^2R^3C=CR^4R^5)^b]_y]}{[[Cu(facac)]_x[R^2R^3C=CR^4R^5)^{m-b}]_y]}$$

where m-b represents any of the other alkene complexes in the mixture, at equivalent partial pressure of alkene is at least about 1.05.

In yet another aspect of the invention, there is provided a process for separating alkadienes from a gaseous mixture containing at least one $C_4$ to $C_{10}$ alkadiene and at least one monoalkene of the formula $R^8R^9C=CR^{10}R^{11}$ where $R^8$ to $R^{11}$ are independently H or $C_1$ to $C_6$ alkyl which comprises: contacting the mixture at a temperature sufficient to maintain the mixture in a gaseous state with a solution of a cuprous fluorinated acetylacetonate complex in an organic solvent, said complex having the formula $[Cu(facac)]_xL_y$ where facac, x, y and L are defined above, wherein the stabilizing agent L is displaced and a mixture of complexes of the formulae $[Cu(facac)]_x(alkadiene)_y$ and $[Cu(facac)]_x$-

(monoalkene)$_y$ is formed; and separating the alkadiene containing complex provided that the loadings in the solution of [[Cu(facac)]$_x$(alkadiene)$_y$] and [[Cu(facac)]$_x$(monoalkene)$_y$] at equivalent partial pressure of alkadiene and monoalkene are different by at least about 5%.

DETAILED DESCRIPTION OF THE INVENTION

When a feedstream containing a gaseous alkene mixture is contacted with a solution of [Cu(facac)]$_x$L$_y$, a reaction occurs whereby L is displaced by alkene. The concentration of any given alkene-containing complex in solution is a function of the complexing ability of that particular alkene. Thus different alkenes are absorbed into and held in solution based on their complexing abilities with the cuprous fluorinated acetylacetonate complex.

In the cuprous fluorinated acetylacetonate complexes of the formula [Cu(facac)]$_x$L$_y$ where facac is R$^6$ is preferably C$_1$-C$_3$ fluoroalkyl, especially CF$_3$, C$_1$-C$_6$ alkyl which may be substituted with phenyl, C$_6$-C$_{10}$ aryl or C$_4$-C$_5$ heterocycle containing O, S or N, especially S, R$^7$ is preferably H with the proviso that R$^6$ and R$^7$ may be joined together to form a C$_6$ ring, n is preferably 1 to 4, especially 1, and x and y are 1 or 2. Examples of preferred embodiments of fluorinated acetylacetones which are incorporated into the cuprous complexes include is especially preferred.

Complexes of the formula [Cu(facac)]$_x$L$_y$ may be prepared by reacting Cu$_2$O and Hfacac (hexafluoroacetylacetone) in the presence of excess stabilizing agent L as solvent. This reaction is exemplified as follows:

[Cu(facac)]$_x$L$_y$ complexes may be isolated from solution. It is preferred, however, to use the complex-containing solution without isolation of complex. Concentrations of complex are not critical and may range from 0.1M to 5M.

When a solution containing the [Cu(facac)]$_x$L$_y$ complex is contacted with a gaseous alkene mixture, alkenes are absorbed into solution and react with cuprous complex by displacing stabilizing agent. In the case of a mixture containing butene-1, butene-2, isobutylene and n-butane, the following equilibria illustrate the displacement reaction and equilibria established:

where in this example facac is hexafluoroacetylacetonate and L is α-methyl styrene.

Figure 1:
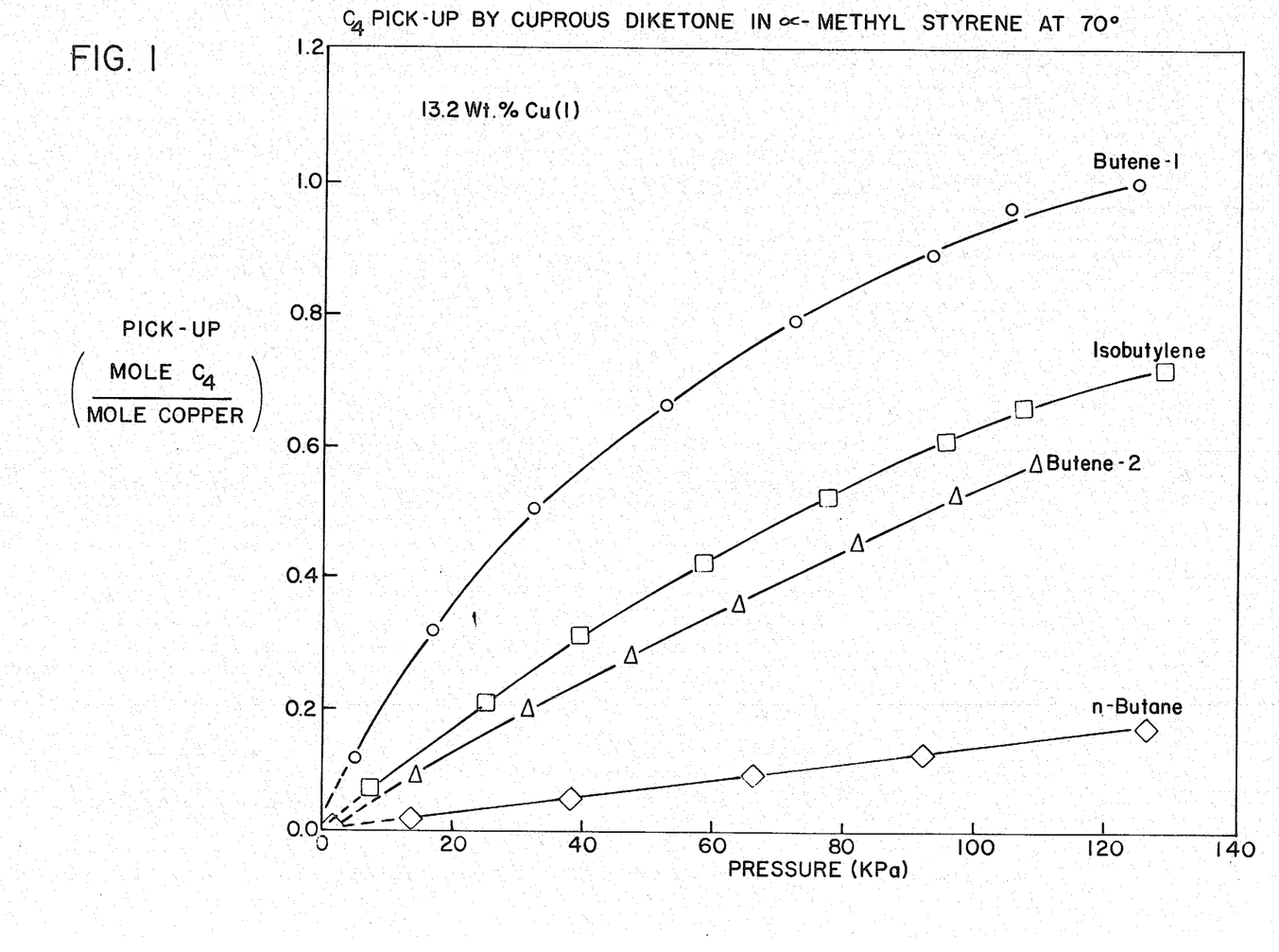
FIG. 1 is a graph of C$_4$ pick-up by Cu(facac) in α-methyl styrene.

In the above-cited example of isomeric butenes, the amount of each butene isomer absorbed into solution by displacement reaction to form a second cuprous complex can be measured as a function of alkene pressure. If a plot is made of individual butene pressure versus butene pick-up, which is defined as the number of moles of individual butene absorbed divided by the number of moles of copper (present as the cuprous complex), FIG. 1 shows that each butene isomer is selectively absorbed according to the strength of the particular cuprous complex formed by displacement. At any equivalent pressure, it can be seen that order of butene pick-up is butene-1 > isobutylene > butene-2.

The separation factor is defined as a ratio of butene pick-up at equivalent partial pressure. Again in reference to FIG. 1, the separation factor for butene-1 and isobutylene is the ratio of $$\frac{\text{(butene-1)}}{\text{(moles Cu)}} \div \frac{\text{(isobutylene)}}{\text{(moles Cu)}} = \frac{[\text{(butene-1)}]}{[\text{(isobutylene)}]}$$

at 100 KPa partial pressure and is expressed in terms of concentration. The separation factor is about 1.5. Other separation factors which can be determined from FIG. 1 are butene-1:butene-2=1.6 and isobutylene:butene-2=1.2. It is noted that FIG. 1 shows a small amount of butane pick-up. This amount, which corresponds to physical absorption into solution, is approximately constant for all isomeric butenes at equivalent partial pressure and is not a consideration in calculating separation factors. In a general case, e.g., a mixture of alkenes of the formulae $CH_2=CHR^1$ and $R^2R^3C=CR^4R^5$, the separation factor at equivalent partial pressure is defined as the ratio of $$\frac{[(CH_2=CHR^1)]}{[(R^2R^3C=CR^4R^5)]}$$

which ratio can be determined from a plot of pick-up for $CH_2=CHR^1$ and $R^2R^3C=CR^4R^5$ versus their respective pressures. Separation factors are preferably at least about 1.05, most preferably at least about 1.1.

The process of the invention is directed to separating linear 1-alkenes from mixtures containing at least one of branched 1-alkenes, linear internal alkenes and branched internal alkenes, separating mixtures of branched 1-alkenes, linear internal alkenes and/or branched internal alkenes, and separating mixtures of mono- and dialkenes. These separations are based on the differing strengths of the various $[Cu(facac)]_x(alkene)_y$ complexes formed.

In the case of separating mixtures containing linear 1-alkenes, preferred linear 1-alkenes have the formula $CH_2=CHR^1$ wherein $R^1$ is H or $C_1$ to $C_4$ alkyl, especially $C_1$ to $C_3$ alkyl. Branched 1-alkenes, linear internal alkenes and branched internal alkenes have the formula $R^2R^3C=CR^4R^5$ where preferred $R^2$ to $R^5$ are independently H or $C_1$ to $C_4$ alkyl, especially $C_1$ to $C_3$ alkyl with the proviso that at least two of $R^2$ to $R^5$ are not H. Alkyl moieties may be substituted with non-reactive substituents such as halogen, nitro and the like. Preferred linear 1-alkenes are ethylene, propylene, butene-1 and pentene-1. Preferred branched 1-alkenes and linear and branched internal alkenes are butene-2, isobutylene, pentene-2, pentene-3, 2-methylbutene-2 and 2,2-dimethylpropene-1. Especially preferred separations include the separation of butene-1 from a $C_4$ mixture and the separation of pentene-1 from a $C_5$ mixture. For mixtures of internal alkenes of the formula $R^2R^3C=CR^4R^5$, preferred separations relate to the separation of isobutylene from butene-2 and the separation of internal pentene isomers.

The present process can also be used to separate alkadienes from monoalkenes. Preferred alkadienes are $C_4$ to $C_7$ alkadienes, especially $C_4$ to $C_6$ alkadienes. Alkadienes having a skeletal arrangement of $C=C-C=C$ and $C=C-C-C=C$ will usually form a bidentate complex with the copper in the cuprous acetylacetonate complex. Such chelated ring configurations are typically more stable than a corresponding monoalkene complex and these differences in stability would be reflected in separation factors. Preferred monoalkenes of the formula $R^8R^9C=CR^{10}R^{11}$ are those wherein $R^8$ and $R^{11}$ are independently H or $C_1$ to $C_4$ alkyl.

The temperature for determining separation factors and separating alkene mixtures is that sufficient to maintain the alkene mixture in contact with organic solvent as a gas phase. $C_2$ to $C_4$ alkenes are normally gases at room temperature. $C_5$ and greater alkenes may require elevated temperatures to maintain the alkenes as gases.

Pressures of individual alkenes in the mixture are in the range of from 1 KPa to 1.000 KPa (100 KPa=1 atm). Once equilibrium between gas phase and liquid phase has been reached for any given alkene, there is generally no advantage to increasing pressure.

Although solvents may be any organic solvent capable of dissolving cuprous complex and absorbing alkene, it is preferred to use the stabilizing agent L as solvent. This is advantageous in the separation and recovery of cuprous fluorinated acetylacetonate complex.

The stabilizing agent prevents any disproportionation reaction of cuprous fluorinated acetylacetonate complex to copper metal when alkene is removed from the cuprous complex. This is illustrated by the following reaction:

The stabilizing agent L is selected such that its boiling point is greater than the reaction temperature, i.e., L should be a liquid at reaction temperatures. L is preferably a high boiling linear or cyclic alkene, alkyne, isonitrile, nitrile or sulfide, more preferably an alkene, alkyne or isonitrile, especially an alkene. Preferred alkenes, alkynes and isonitriles are (a) alkenes of the formula where each $R^{12}$–$R^{15}$ is independently H provided that at least one of $R^{12}$–$R^{15}$ is not H; $C_1$–$C_{30}$, more preferably $C_1$–$C_{15}$ and especially $C_1$–$C_8$ aliphatic with the proviso that any combination of $R^{12}$, $R^{13}$, $R^{14}$ and $R^{15}$ may be joined together to form at least one $C_5$–$C_{14}$, more preferably $C_6$–$C_{12}$, most preferably $C_6$–$C_8$ cycloaliphatic ring; —C≡N; $C_6$–$C_{10}$ aryl; $C_7$–$C_{14}$ araliphatic;

where q and p are 0 or 1, $R^{16}$ is $C_1$–$C_{20}$, preferably $C_1$–$C_{10}$ aliphatic, and $R^{17}$ is H, $C_1$–$C_{10}$ aliphatic or $C_6$–$C_{10}$ aryl with the proviso that adjacent may be joined together to form a $C_4$–$C_{16}$ anhydride; (b) alkynes of the formula $R^{18}—C≡C—R^{19}$ where $R^{18}$ and $R^{19}$ are independently H with the proviso that both $R^{18}$ and $R^{19}$ cannot be H; $C_1$–$C_{30}$, more preferably $C_1$–$C_{15}$ and especially $C_1$–$C_8$ aliphatic; $C_6$–$C_{10}$ aryl or $C_7$–$C_{14}$ araliphatic; and (c) isonitriles of the formula $R^{20}-N\equiv C$ where $R^{20}$ is $C_1$-$C_{20}$, preferably $C_1$-$C_{10}$ aliphatic; $C_3$-$C_{10}$, preferably $C_5$-$C_7$ cycloaliphatic; $C_7$-$C_{20}$, preferably $C_7$-$C_{14}$ araliphatic or $C_6$-$C_{10}$ aryl. The aliphatic, cycloaliphatic, araliphatic and aryl hydrocarbyl radicals may be substituted with unreactive substituents such as halogen, alkoxy, nitro and the like, and the aliphatic, cycloaliphatic or araliphatic hydrocarbyl radicals may be saturated or unsaturated.

Nitriles and sulfides are of the formulae $R^{21}-C\equiv N$ and $R^{22}-S-R^{23}$ where $R^{21}$, $R^{22}$ and $R^{23}$ are independently $C_1$-$C_{20}$, preferably $C_1$-$C_{20}$ aliphatic; $C_3$-$C_{10}$, preferably $C_5$-$C_7$ cycloaliphatic; $C_7$-$C_{20}$, preferably $C_7$-$C_{14}$ araliphatic or $C_6$-$C_{10}$ aryl.

Most preferred stabilizing agents are $C_6$-$C_{20}$ alkenes. Examples of suitable alkenes include: 1-octene, limonene, 1,5-cyclooctadiene, stilbene, betapinene, 1-dodecene, styrene, cyclooctene, 1,5,9-cyclododecatriene, 2,4,4-trimethyl-1-pentene, 1-decene, 1-tetradecene, 1,5-bicycloheptadiene, 1-octadecene, octalin, methylene cyclohexane, diphenyl fulvene, benzyl cinnamate, methyl cyclopentadiene dimer, di-n-butyl maleate, maleic anhydride, oleic acid, linolenic acid, alpha-methyl styrene and diethyl maleate.

Figure 2:
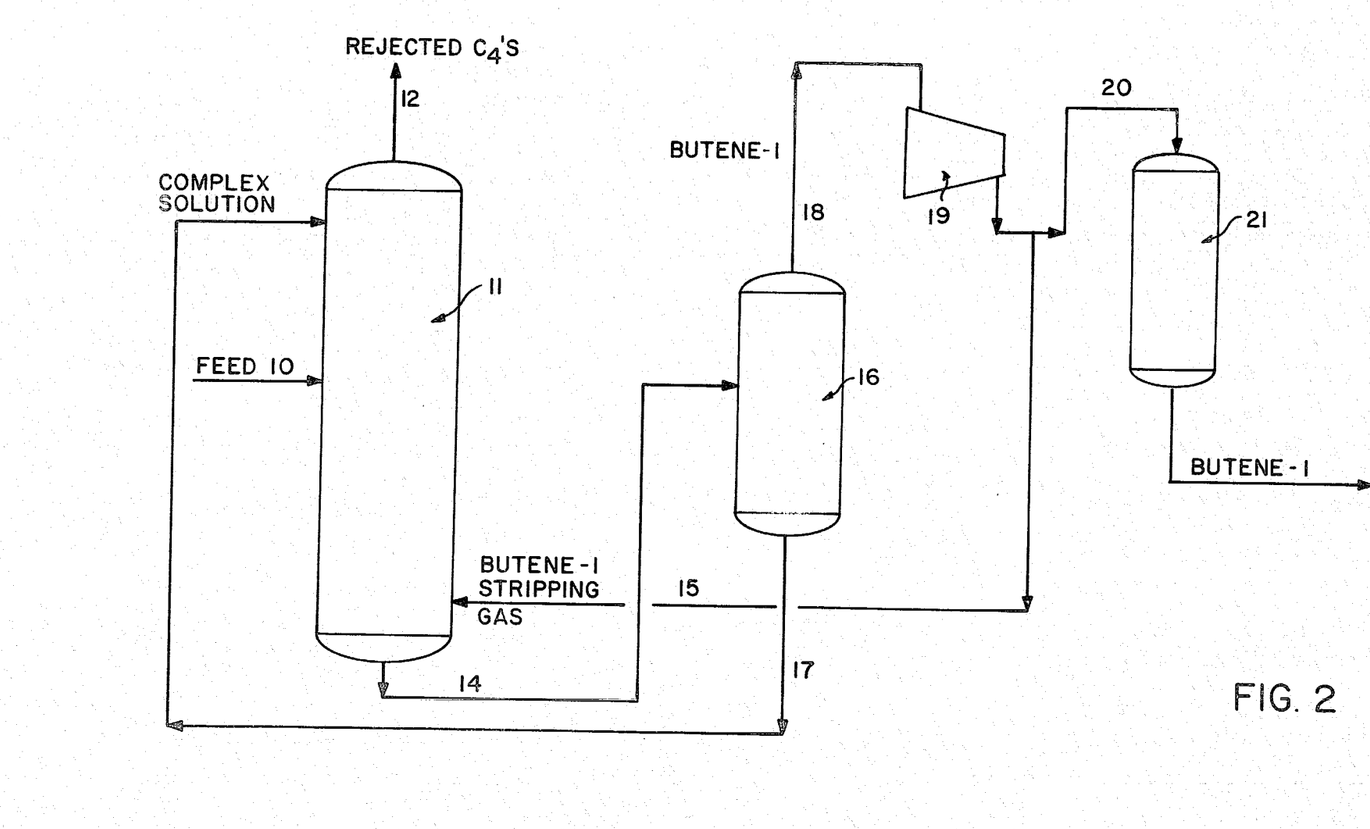
FIG. 2 is a schematic drawing showing the separation of butene-1 from a C$_4$ feed.

While the process of the invention may be carried out in a batch or continuous mode, a continuous mode of operation is preferred. FIG. 2 is a schematic representation of a preferred embodiment for separating a $C_4$ mixture. Feedstream containing the butene/butane mixture is contacted through line 10 with a solution of cuprous fluorinated acetylacetonate in a countercurrent extractor 11. A gas mixture of uncomplexed butenes and butanes and depleted in butene-1 content is withdrawn through line 12 while a butene-1 rich extract is withdrawn through line 14. A butene-1 stripping gas is added through line 15 to convert any butene-2 or isobutylene complexes to butene-1 complex. The butene-1 rich extract is conducted to a separation zone 16 where it is heated to about 150° C. in the presence of stabilizing agent. Butene-1 is removed from complex by heat and is replaced by stabilizing agent L thereby reforming [Cu(facac)]$_x$L$_y$ which is recycled to the extraction zone through line 17. Separated butene-1 is removed through line 18. Separation zone 16 may be a series of heated drums wherein the pressure is reduced to below 1 atm. The separated butene-1 is fed to a compressor 19. A portion of the butene-1 is recycled to extraction zone 11 through 15 while the major portion is conducted through line 20 to a carbon adsorption zone 21. The carbon adsorption zone removes any remaining traces of solvent.

The alkene mixtures to be separated may contain inert gases such as alkanes, $CO_2$, $N_2$ and the like. Strongly oxidizing or complexing gases such as $O_2$ or CO should not be present in amounts greater than about 5 vol %.

The invention is further illustrated by the following examples.

EXAMPLE 1

The general procedure is described in the following manner. Measurements were made in an apparatus consisting of a source vessel and a reactor vessel. Both vessels are thermostated and are interconnected. In the actual experiment, the source vessel, whose volume is precisely known, is evacuated, then filled with a gas whose absorption is to be measured. The reactor vessel whose volume is also precisely known, is evacuated then partially filled with a weighed amount of a solution of the Cu diketonate complex. Both the density and copper content of this solution are known. Therefore, the number of moles of copper can be calculated as well as the free volume above the liquid in the reactor vessel. The reactor vessel is then pumped down to the vapor pressure of the solvent, and a sample of gas is introduced from the source vessel into the reactor vessel. By measuring the pressure in the source vessel before and after the addition, the exact weight or number of moles of gas added can be calculated. After a given length of time or after equilibrium has been reached, the vapor pressure in the reactor vessel is recorded. After correcting for the solvent vapor pressure, the moles of gas in the vapor phase can be calculated by the usual gas equations, and the number of moles in the liquid phase is taken as the difference between the total moles added and the moles in the vapor phase. Since the amount of copper in solution is known, one can easily calculate the moles of gas absorbed per mole of Cu. Additional increments of gas are added from the source to the reactor allowing one to plot the moles of gas absorbed per mole of copper vs. pressure over a fairly wide pressure range. Both the source and reactor vessels are then evacuated to prepare for the measurement of the next gas. The source vessel is then filled with the new gas, and the above procedure is repeated. The separation factor between the two gases is calculated as the number of moles of the gas picked up per mole of Cu for one of the two gases divided by that of the second gas both taken at the same partial pressure of overhead gas.

In this experiment, the pick-up of a number of $C_4$ hydrocarbons including 1-butene, 2-butene, n-butane and isobutylene, by a solution of Cu(hfacac) (hfacac=hexafluoroacetylacetonate) in α-methylstyrene (containing 13.2% Cu), was measured. The solution was prepared by reacting $Cu_2O$ and hexafluoroacetylacetone in the presence of α-methyl styrene as solvent. The results are plotted in FIG. 1. By using this pure component data, a butene-1/butene-2 separation factor of 1.6 at 100 kPa can be calculated. The separation factor for butene-1/isobutylene is calculated to be 1.5, also at 100 kPa.

EXAMPLE 2

Similar experiments were carried out in a number of different solvents. The results are shown in Table I.

EXAMPLE 3

Figure 3:
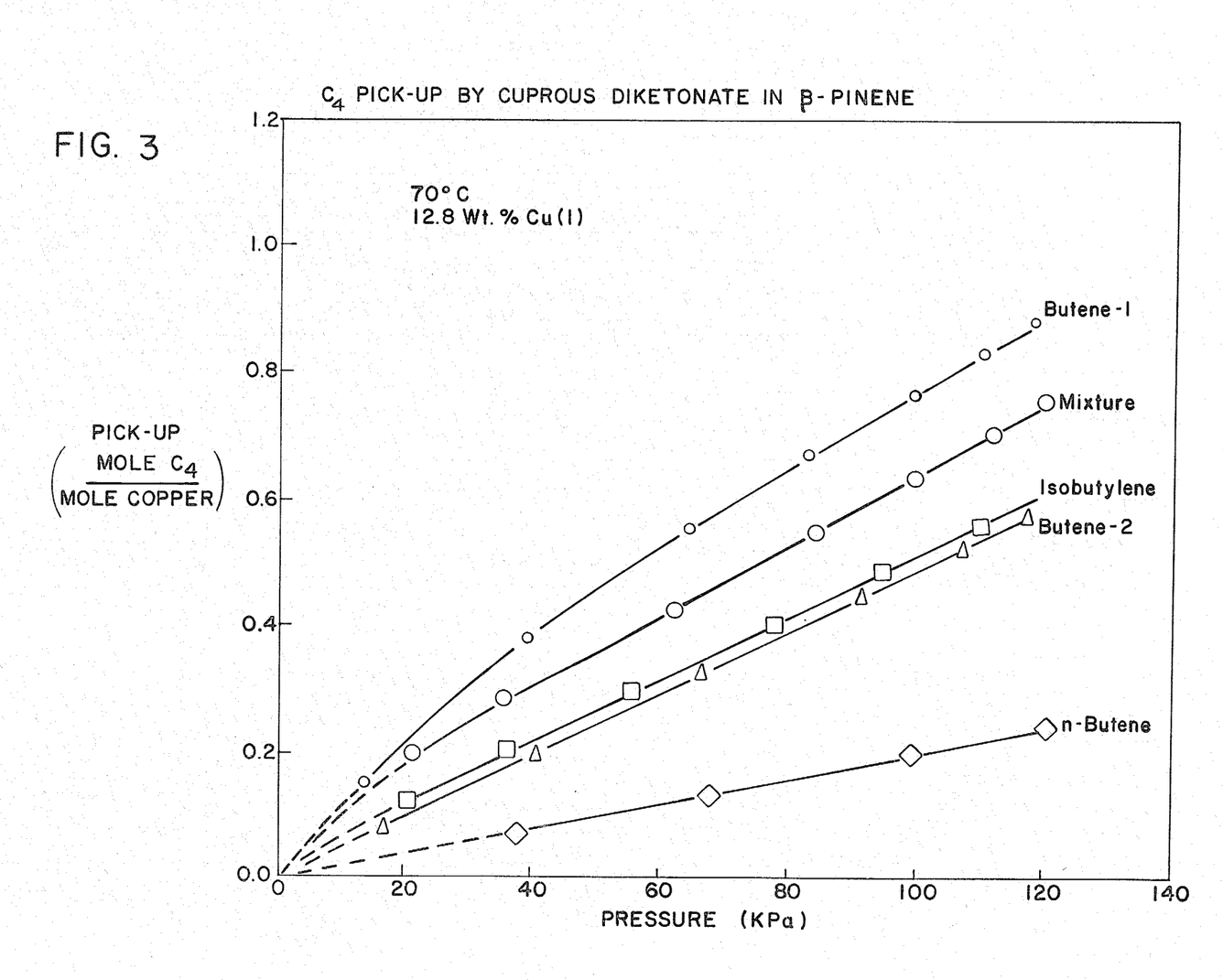
FIG. 3 is a graph of C$_4$ pick-up by Cu(facac) in β-pinene.

A further experiment was carried out using a solution of Cu(hfacac) in β-pinene containing 12.8% Cu. In addition to measuring the pick-up of the pure components, 1-butene, 2-butene, isobutylene and n-butane, the pick-up of a mixture containing 42.6% 1-butene, 38.4% isobutylene and 19.0% 2-butene was also measured. The results are shown in FIG. 3. The final gas composition at equilibrium above the solution was found to be 34.5% 1-butene, 50.0% isobutylene and 15.5% 2-butene. The separation factors measured and calculated from the pure component data are shown in Table II. This experiment demonstrates that isomeric alkenes can effectively be separated from mixtures and that the separation factors can be calculated from pure component data.

TABLE I

Butene-1/Butene-2 Separation Factors for Cuprous Diketonate Solutions in Various Solvents

| Solvent | Cuprous Concentration Wt. % | Butene-1 Pickup* (Mole/Mole Copper) | Butene-1/Butene-2* Separation Factor |
|---|---|---|---|
| Diethyl-Maleate | 2.9 | 1.4 | 3.0 |
| Di-n-Butyl-Maleate | 6.7 | 1.4 | 1.5 |
| 2,4,4-Trimethyl-1-Pentene | 13.5 | 0.5 | 1.3 |
| Methyl Cyclopentadiene Dimer | 13.4 | 0.5 | 1.5 |
| Limonene (Dipentene) | 15.1 | 0.8 | 1.5 |
| α-Methyl Sytrene | 13.2 | 1.0 | 1.6 |
| β-Pinene | 12.8 | 0.9 | 1.6 |

*120 KPa, 70° C.

TABLE II

Separation of Butene Mixture

| Method of Determination | Butene-1/Butene-2 Separation Factor | Butene-1/Isobutylene Separation Factor | Pick up of Butenes (Mole/Mole Copper) |
|---|---|---|---|
| Measurement of Mixture* | 1.7 | 1.7 | 0.77 |
| Calculation from Pure Component Measurements | 1.6 | 1.5 | 0.78 |

*120 KPa, 70° C.
34.5% Butene-1, 50.0% Isobutylene, 15.5% Butene-2.

EXAMPLE 4

Figure 4:
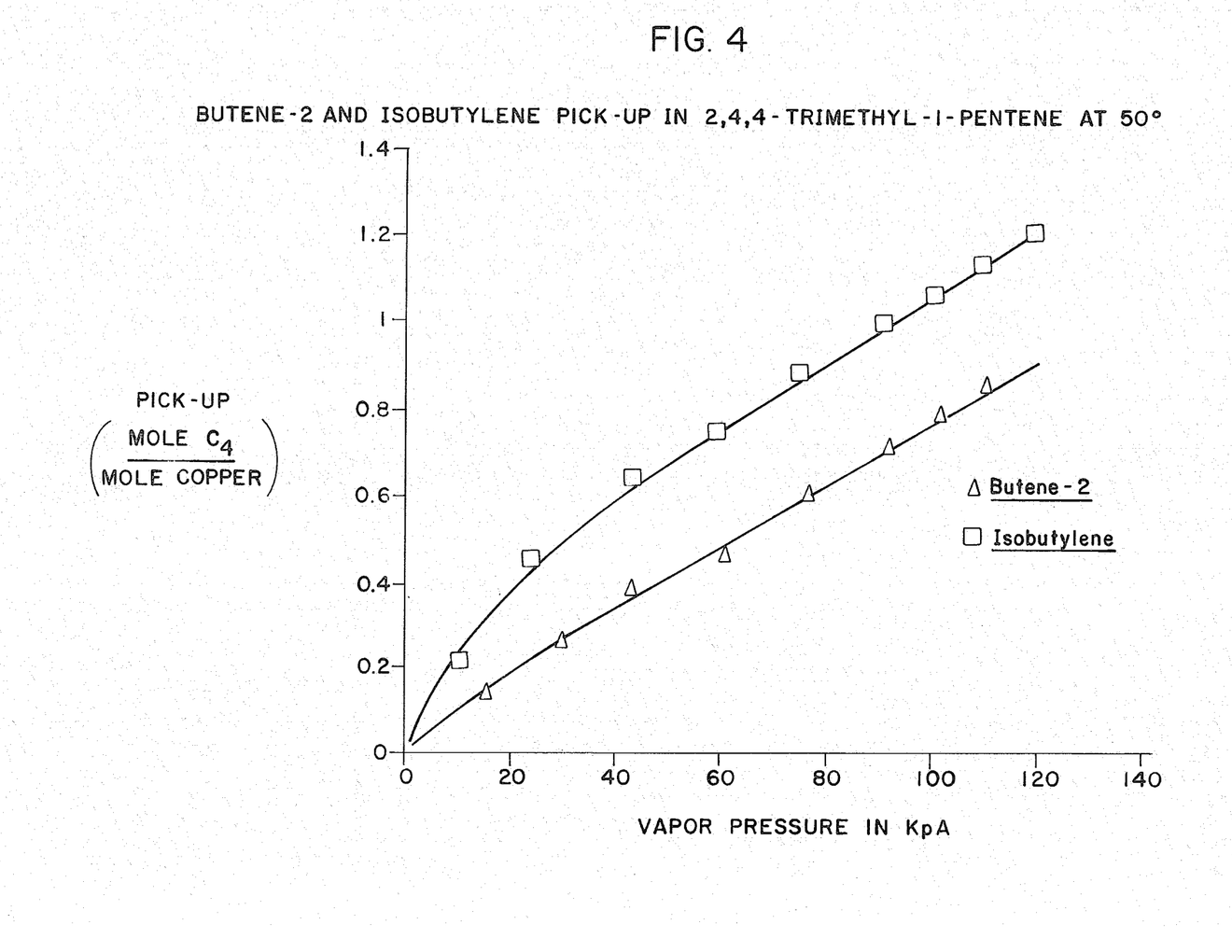
FIG. 4 is a graph of butene-2 and isobutylene pick-up by Cu(facac) in 2,4,4-trimethyl-1-pentene.

In this experiment, the pick-up of 2-methylpropene and 2-butene, by a solution of Cu(hfacac) in 2,4,4-trimethyl-1-pentene containing 13.5% Cu, was measured. The results are shown in FIG. 4. The separation factor in this case is approximately 1.4 at 100 kPa, showing that a branched alkene can be separated from a linear internal alkene.

EXAMPLE 5

This example illustrates the separation of 1-pentene from a mixture of $C_5$ hydrocarbons. The mixture is a commercial isoprene raffinate with the following composition: 1-pentene, 22.0%, 2-pentene, 16.2%; 2-methyl-1-butene, 20.2%; 3-methyl-1-butene, 5.3%; 2-methyl-2-butene, 3.9%, isoprene, 2.4%,; 1,4-pentadiene, 4.6%; n-pentane, 10.3% isopentane, 7.8%; 1,3-pentadiene 2.3%; and smaller amounts of various other $C_5$ hydrocarbons. This mixture was contacted with a solution of the Cu(I) hexafluoracetylacetonate complex in α-methyl styrene at 90° C. in the manner described in Example 1. A measurement of the composition of the gas phase at a total pressure of 80 kPa allowed calculation of the partial pressure of many of the individual components. This along with the pick-up of these components and separation factors for 1-pentene/$C_5$ gas component are given in Table III. These data show that 1-pentene can effectively be separated from a complex $C_5$ hydrocarbon mixture using the Cu(I) hexafluoroacetylacetonate complex.

TABLE III

Separation of Isoprene Raffinate by Cuprous Diketonate in α-Methyl Styrene*

| Gas Component | Partial Pressure (KPa) | Pick-up Mole Mole Copper | Separation Factor for 1-Pentene/ Gas Component |
|---|---|---|---|
| 1-Pentene | 12.3 | 0.147 | 1.0 |
| 2-Pentene | 12.0 | 0.095 | 1.5 |
| 2-Methyl-1-Butene | 16.5 | 0.123 | 1.6 |
| 3-Methyl-1-Butene | 3.5 | 0.031 | 1.4 |
| 2-Methyl-2-Butene | 3.7 | 0.022 | 2.0 |
| Isoprene | 1.5 | 0.015 | 1.2 |
| Pentane | 28.4 | 0.102 | 3.3 |

*90° C., 80 KPa

What is claimed is:
1. A process for separating a gaseous mixture comprising at least one linear 1-alkene of the formula $CH_2=CHR^1$ where $R^1$ is H or $C_1-C_6$ alkyl and at least one other alkene of the formula $R^2R^3C=CR^4R^5$ where $R^2$ to $R^5$ are independently H or $C_1-C_6$ alkyl with the proviso that at least two of $R^2$ to $R^5$ are not H, into a fraction relatively rich in the linear 1-alkene and into a fraction relatively deficient in the linear 1-alkene, said process comprising:

contacting the alkene mixture at a temperature sufficient to maintain the mixture in a gaseous state with a solution of a cuprous fluorinated acetylacetonate complex in an organic solvent, said complex having the formula $[Cu(facac)]_xL_y$ where facac is $R^6$ is $C_1-C_6$ fluoralkyl, $C_1-C_8$ alkyl, $C_4-C_6$ heterocycle containing O, S or N or $C_6-C_{10}$ aryl, $R^7$ is H or $C_1-C_6$ alkyl with the proviso that $R^6$ and $R^7$ together with the carbons to which they are attached may be joined together to form a $C_6$ ring, n is an integer from 1 to 8, x and y are 1 or 2 and L is a stabilizing agent, said stabilizing agent being an unsaturated compound containing at least one non-aromatic unsaturation and being a liquid at the reaction temperature, wherein the stabilizing agent L is displaced and a mixture of complexes of the formulae $[Cu(facac)]_x(CH_2=CHR^1)_y$ and $[Cu(facac)]_x(R^2R^3C=CR^4R^5)_y$ is formed; and separating the complex of the formula $[Cu(facac)]_x(CH_2=CHR^1)_y$ provided that the separation factor defined as the ratio of $$\frac{[[Cu(facac)]_x(CH_2=CHR^1)_y]}{[[Cu(facac)]_x(R^2R^3C=CR^4R^5)_y]}$$

at equivalent partial pressure of alkene is at least about 1.05.

2. A process for separating a gaseous mixture of alkenes of the formula $(R^2R^3C=CR^4R^5)^m$ where $R^2$ to $R^5$ are independently H or $C_1$ to $C_6$ alkyl with the proviso that at least two of $R^2$ to $R^5$ are not H, and m is the number of different alkenes in the mixture which comprises:

contacting the alkene mixture at a temperature sufficient to maintain the mixture in a gaseous state with a solution of a cuprous fluorinated acetylacetonate complex in an organic solvent, said complex having the formula $[Cu(facac)]_xL_y$ where facac is $$R^6-\overset{O}{\overset{\|}{C}}-\overset{R^7}{\overset{|}{C}}-\overset{O}{\overset{\|}{C}}-C_nF_{2n+1},$$

$R^6$ is $C_1-C_6$ fluoralkyl, $C_1-C_8$ alkyl, $C_4-C_6$ heterocycle containing O, S or N or $C_6-C_{10}$ aryl, $R^7$ is H or $C_1-C_6$ alkyl with the proviso that $R^6$ and $R^7$ together with the carbons to which they are attached may be joined together to form a $C_6$ ring, n is an integer from 1 to 8, x and y are 1 or 2 and L is a stabilizing agent, said stabilizing agent being an unsaturated compound containing at least one non-aromatic unsaturation and being a liquid at the reaction temperature, wherein the stabilizing agent L is displaced and a mixture of m complexes of the formulae $[Cu(facac)]_x[(R^2R^3C=CR^4R^5)^b]_y$ and $[Cu(facac)]_x[R^2R^3C=CR^4R^5)^{m-b}]_y$ are formed where b represents one complex in the set of m complexes formed; and separating a complex of the formula $[Cu(facac)]_x[(R^2R^3C=CR^4R^5)^b]_y$ provided that the separation factor defined as the ratio of $$\frac{[[Cu(facac)]_x[(R^2R^3C=CR^4R^5)^b]_y]}{[[Cu(facac)]_x[R^2R^3C=CR^4R^5)^{m-b}]_y]}$$

where m-b represents any of the other alkene complexes in the mixture, at equivalent partial pressure of alkene is at least about 1.05.

3. The process of claims 1 or 2 wherein the separation factor is at least about 1.1.

4. The process of claims 1 or 2 wherein the stabilizing agent is a linear or cyclic alkene, alkyne, isonitrile, nitrile or sulfide.

5. The process of claims 1 or 2 wherein the stabilizing agent is a $C_6-C_{20}$ linear or cyclic alkene.

6. The process of claims 1 or 2 wherein the gaseous mixture contains $C_4-C_5$ alkenes.

7. The process of claim 7 wherein the gaseous mixture contains at least two of 1-butene, 2-butene and isobutylene.

8. The process of claim 8 wherein 1-butene is separated from at least one of 2-butene and isobutylene.

9. The process of claims 1 or 2 wherein the stabilizing agent functions as the organic solvent.

10. A process for separating 1-butene from a gaseous $C_4$ hydrocarbon mixture or for separating 1-pentene from a gaseous $C_5$ hydrocarbon mixture, which comprises:

contacting the $C_4$ or $C_5$ hydrocarbon mixture at a temperature sufficient to maintain the mixture in a gaseous state with a solution of a cuprous fluorinated acetylacetonate complex in an organic solvent, said complex having the formula $[Cu(facac)]_xL_y$ where facac is $$R^6-\overset{O}{\overset{\|}{C}}-\overset{R^7}{\overset{|}{C}}-\overset{O}{\overset{\|}{C}}-C_nF_{2n+1},$$

$R^6$ is $C_1-C_6$ fluoralkyl, $C_1-C_8$ alkyl, $C_4-C_6$ heterocycle containing O, S or N or $C_6-C_{10}$ aryl, $R^7$ is H or $C_1-C_6$ alkyl with the proviso that $R^6$ and $R^7$ together with the carbons to which they are attached may be joined together to form a $C_6$ ring, n is an integer from 1 to 8, x and y are 1 or 2 and L is a stabilizing agent, said stabilizing agent being an unsaturated compound containing at least one non-aromatic unsaturation and being a liquid at the reaction temperature, wherein the stabilizing agent L is dispatched and a mixture of complexes of the formulae $[Cu(facac)]_x(1\text{-butene})_y$ and $[Cu(facac)]_x(C_4\text{ hydrocarbon})_y$ or a mixture of complexes of the formulae $[Cu(facac)]_x(1\text{-pentene})_y$ and $[Cu(facac)]_x(C_5\text{ hydrocarbon})_y$ is formed; and separating the complex of the formula $[Cu(facac)]_x(1\text{-butene})_y$ or $[Cu(facac)]_x(1\text{-pentene})_y$ provided that the separation factor defined as the ratio of $$\frac{[[Cu(facac)]_x(1\text{-butene})_y]}{[[Cu(facac)]_x(C_4\text{ hydrocarbon})_y]}$$

or $$\frac{[[Cu(facac)]_x(1\text{-pentene})_y]}{[[Cu(facac)]_x(C_5\text{ hydrocarbon})_y]}$$

at equivalent partial pressure of alkene is at least about 1.05.

11. A process for separating a gaseous mixture comprising at least one $C_4$ to $C_{10}$ alkadiene and at least one monoalkene of the formula $R^8R^9C=CR^{10}R^{11}$ where $R^8$ to $R^{11}$ are independently H or $C_1-C_6$ alkyl into a fraction relatively rich in the alkadiene and a fraction relatively deficient in the alkadiene, said process comprising:

contacting the mixture at a temperature sufficient to maintain the mixture in a gaseous state with a solution of a cuprous fluorinated acetylacetonate complex in an organic solvent, said complex having the formula $[Cu(facac)]_xL_y$ where facac is $R^6$ is $C_1$-$C_6$ fluoralkyl, $C_1$-$C_8$ alkyl, $C_4$-$C_6$ heterocycle containing O, S or N or $C_6$-$C_{10}$ aryl, $R^7$ is H or $C_1$-$C_6$ alkyl with the proviso that $R^6$ and $R^7$ together with the carbons to which they are attached may be joined together to form a $C_6$ ring, n is an integer from 1 to 8, x and y are 1 or 2 and L is a stabilizing agent, said stabilizing agent being an unsaturated compound containing at least one non-aromatic unsaturation and being a liquid at the reaction temperature, wherein the stabilizing agent L is displaced and a mixture of complexes of the formulae

[Cu(facac)]$_x$(alkadiene)$_y$ and

[Cu(facac)]$_x$(monoalkene)$_y$ is formed; and separating the alkadiene containing complex provided that the loadings in the solution of [[Cu(facac)]$_x$(alkadiene)$_y$] and [[Cu(facac)]$_x$(monoalkene)$_y$] at equivalent partial pressure of alkadiene and monoalkene are different by at least about 5%.

* * * * *